United States Patent [19]

Desbois

[11] Patent Number: 4,695,657

[45] Date of Patent: Sep. 22, 1987

[54] PROCESS FOR PREPARING COMPOUNDS CONTAINING A DIFLUOROMETHYLENE GROUP IN A POSITION α TO AN OXYGEN ATOM

[75] Inventor: Michel Desbois, Rilleux, France

[73] Assignee: Rhone-Poulenc Specialites Chimiques, Courbevoie, France

[21] Appl. No.: 809,721

[22] Filed: Dec. 17, 1985

[30] Foreign Application Priority Data

Dec. 26, 1984 [FR] France ............................... 84 19798

[51] Int. Cl.$^4$ ...................... C07C 43/02; C07C 43/18; C07C 69/63; C07C 69/62
[52] U.S. Cl. .................................. 568/656; 560/138; 560/141; 560/142; 560/144; 560/145; 560/227; 564/442; 568/54; 568/433; 568/588; 568/639; 568/642; 568/649; 568/655; 568/683
[58] Field of Search ................ 570/165, 127; 568/655, 568/656, 649, 588, 639, 642, 51, 433, 842, 54, 683; 560/145, 227; 564/442

[56] References Cited

U.S. PATENT DOCUMENTS 2,567,569 9/1951 McBee et al. .................. 568/655 X
4,093,665 6/1978 Belous et al. .................. 568/656 X

OTHER PUBLICATIONS

Prober, Jour. Amer. Chem. Soc. 75 (1953), 968–973.

*Primary Examiner*—James H. Reamer
*Assistant Examiner*—Patricia M. Scott
*Attorney, Agent, or Firm*—Finnegan, Henderson, Farabow, Garrett & Dunner

[57] ABSTRACT

A process for the preparation of compounds containing a difluoromethylene group in a position α to an oxygen atom. An alcohol or a phenol is brought into contact with trifluoroacetic acid or a halide or anhydride thereof in anhydrous liquid hydrofluoric acid, in the presence of boron trifluoride, in a quantity such that the absolute pressure of boron trifluoride is at least about one bar. The compounds obtained according to the invention are used as synthesis intermediates in the pharmaceutical, plant-protection, and dye industries, as anesthetics and as additives for lubricating oils.

8 Claims, No Drawings

PROCESS FOR PREPARING COMPOUNDS CONTAINING A DIFLUOROMETHYLENE GROUP IN A POSITION α TO AN OXYGEN ATOM

The present invention relates to a process for the preparation of compounds containing a difluoromethylene group in a position α to an oxygen atom and more particularly to a process for simultaneous esterification and fluorination to prepare compounds containing a difluoromethylene group in a position α to oxygen.

From British Pat. No. 1,077,547 it is known to esterify fatty diacids with an alcohol in a medium consisting of liquid hydrofluoric acid. The ester is obtained in good yields, but no trace is obtained of derivatives containing a difluoromethylene group in a position α to oxygen.

According to Topchiev, in "Boron Fluoride and its Compounds as Catalysts in Organic Chemistry," USSR Academy of Sciences, it is also known to prepare esters by condensing carboxylic acids and alcohols in the presence of boron trifluoride. The ester is obtained in variable yields, depending on the nature of the acid, but no trace of compounds containing a difluoromethyleneoxy group is obtained.

The prior art thus does not suggest any solution to the problem of preparing derivatives containing a difluoromethyleneoxy group from the corresponding acids and alcohols.

The present invention overcomes the disadvantages of the prior art by providing a process for the preparation of compounds containing a difluoromethyleneoxy group by simultaneous esterification and fluorination, in which an alcohol or a phenol is brought into contact with a carbonyl-containing compound selected from the group consisting of trifluoroacetic acid, halides of trifluoroacetic acid and the anhydride of trifluoroacetic acid, in anhydrous liquid hydrofluoric acid, in the presence of boron trifluoride in a quantity such that the absolute pressure of boron trifluoride is at least about one bar and for a time sufficient to create a difluoromethyleneoxy group by converting at least one carbonyl group of the carbonyl-containing compound to a difluoromethylene group and also be esterifying the at least one carbonyl group with the alcohol or phenol.

Illustrative alcohols and phenols include aliphatic or aromatic alcohols, phenols and phenolic derivatives, which are defined to include any phenol having an aromatic nucleus substituted by a halogen or an alkyl, preferably $C_1$–$C_6$ alkyl, alkoxy, preferably $C_1$–$C_6$ alkoxy, thioalkyl, preferably $C_1$–$C_6$ thioalkyl, phenyl, phenoxy, nitro, amino or carbonyl group.

The molar ratio of trifluoroacetic acid, its halide or its anhydride, to the phenol or to the alcohol is preferably from about 0.5 to 2, more preferably at least about one.

It is preferable to work with a quantity of $BF_3$ such that the absolute pressure of $BF_3$ in the reaction system is from about 5 to 50 bars.

Advantageously, the molar ratio of hydrofluoric acid to the trifluoroacetic acid or halide or anhydride thereof is from about 5 to 50, more preferably, form 10 to 30.

The reaction temperature is preferably from about 0° to 150° C., more preferably from 20° to 80° C.

The reaction may take place in the presence of solvents for the carbonyl-containing compound and/or for the compound containing a difluoromethylene group in a position α to oxygen. Illustrative solvents include $CCl_4$, $CHCl_3$, and $CFCl_2$–$CF_2Cl$.

The following illustrative compounds are among those obtained according to the process of the invention:

Pentafluoroethoxybenzene, 4-chloropentafluoroethoxybenzene, α,α-difluoro-β,β,β-trichloroethoxybenzene, 4-nitropentafluoroethoxybenzene, 4-phenoxypentafluoroethoxybenzene, 4-fluoropentafluoroethoxybenzene, 3-trifluoromethylpentafluoroethoxybenzene, 4-trifluoromethylpentafluoroethoxybenzene, 2-chloro-4-trifluoromethylpentafluoroethoxybenzene, 4-trifluoromethoxypentafluoroethoxybenzene and pentafluoroethyl β,β,β-trifluoroethyl ether.

The compounds produced by the process of the invention are used as synthesis intermediates in the pharmaceutical or plantprotection industries, as anesthetics (Kirk-Othmer II, pp. 684–689) or as additives for lubricating oils.

The compounds produced by the process of the invention may be separated from reaction byproducts and/or unreacted starting materials by means well-known to those skilled in the art, such as gas phase chromatography, as illustrated in the Examples below, and chemical means.

The invention will be described in further detail in the following illustrative, non-limiting Examples.

EXAMPLE 1

50 g (2.5 mol) of anhydrous HF, 12.9 g (0.1 mol) of p-chlorophenol and 22.8 g (0.2 mol) of trifluoroacetic acid are successively introduced into a 250-ml stainless steel reactor. The reactor is closed, filled with gaseous $BF_3$ to a pressure of 20 bars at 20° C., and heated at 70° C. for 18 hours. After cooling and pressure release, the crude acid mixture is poured onto 200 g of crushed ice and is extracted with $CH_2Cl_2$ (3×100 ml). The organic phases are combined, washed with 100 ml of demineralized water and are dried. Analysis by gas phase chromatography and mass spectrometry gives the following composition:

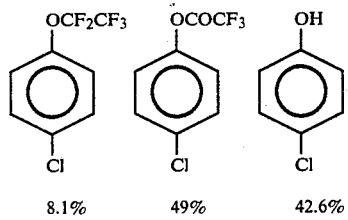

COMPARATIVE EXAMPLE 1A

Using the procedure in Example 1, the following are placed in contact:
12.9 g (0.1 mol) of para-chlorophenol
57 g (0.5 mol) of trifluoroacetic acid. No anhydrous liquid hydrofluoric acid is used.

The reactor is pressurized with 19 bars of $BF_3$ at 14° C. and is heated to 80° C. for 2 h 30 min at a maximum pressure of 24 bars. After analysis by gas phase chromatography combined with mass spectrometry, 79.8% of p-chlorophenyl trifluoroacetate and 20.2% of para-chloro phenol are obtained, and no trace of para-chloropentafluoroethoxybenzene is detected.

COMPARATIVE EXAMPLE 1B

Using the procedure of Example 1, the following are placed in contact:

12.9 g (0.1 mol) of p-chlorophenol
22.8 g (0.2 mol) of trifluoroacetic acid
100 g (5 mol) of anhydrous hydrofluoric acid. No boron trifluoride is used.

The mixture is heated at 80° C. for 23 h 30 min at a maximum pressure of 5 bars. After analysis by gas phase chromatography combined with mass spectrometry, 26.9% of p-chlorophenyl trifluoroacetate and 66.7% of para-chlorophenol are obtained, and no trace of para-chloropentafluoroethoxybenzede is detected.

EXAMPLE 2

The procedure is the same as in Example 1, with the following materials and conditions:

| | |
|---|---|
| OH–C₆H₄–Cl | 0.1 mole = 12.9 g |
| (CF₃CO)₂O | 0.1 mole = 21 g |
| HF | 2.5 moles = 50 g |
| BF₃ | 25 bars at 3° C. |
| T° | 20° C. |
| Time | 18 h 30 min |

After treatment, combined analyses by gas phase chromatography and mass spectrometry show the presence of 4-chloropentafluoroethoxybenzene.

EXAMPLE 3

The procedure is the same as in Example 1, with the following materials and conditions:

| | |
|---|---|
| OH–C₆H₄–F | 0.3 mole = 33.6 g |
| CF₃COOH | 0.3 mole = 34.2 g |
| HF | 5 moles = 100 g |
| BF₃ | 30 bars at 20° C. |
| T° | 50° C. |
| Time | 8 hours. |

After treatments, combined analyses by gas phase chromatography and mass spectrometry show the presence of 4-fluoropentafluoroethoxybenzene.

EXAMPLE 4

The procedure is the same as in Example 1, with the following materials and conditions:

| | |
|---|---|
| CF₃–C₆H₄–OH | 0.2 mole = 32.4 g |
| CF₃COOH | 0.3 mole |
| HF | 5 moles = 100 g |
| BF₃ | 50 bars at 10° C. |
| T° | 20° C. |
| Time | 22 hours. |

After treatment, combined analyses by gas phase chromatography and mass spectrometry show the presence of 3-trifluoromethylpentafluoroethoxybenzene.

What is claimed is:

1. A process for the preparation of an ether compound containing a difluoromethyleneoxy group by simultaneous esterification and fluorination, comprising the step of contacting an alcohol or a phenol with a carbonyl-containing compound selected from the group consisting of trifluoroacetic acid, halides of trifluoroacetic acid and the anhydride of trifluoroacetic acid, in anhydrous liquid hydrofluoric acid, in the presence of boron trifluoride in a quantity such that the absolute of boron trifluoride is at leats about one bar for a time sufficient to create said difluoromethyleneoxy group.

2. The process of claim 1, wherein the molar ratio of hydrofluoric acid to said carbonyl-containing compound is about 5 to 50.

3. The process of claim 2, wherein said molar ratio is 10 to 30.

4. The process of claim 1, wherein said boron trifluoride is used at an absolute pressure of about 50 to 50 bars.

5. The process of claim 1, wherein the reaction temperature ranges from about 0° to 150°C.

6. The process of claim 5, wherein said temperature ranges from 20° to 80° C.

7. The process of claim 1, wherein solvent for one or both of said carbonyl-containing compound and said compound containing a difluoromethyleneoxy group is included.

8. The process of claim 7, wherein the solvent is selected from the group consisting of CCl₄, CHCl₃ and CFCl₂–CClF₂.

* * * * *

UNITED STATES PATENT AND TRADEMARK OFFICE
CERTIFICATE OF CORRECTION

PATENT NO. : 4,695,657
DATED : September 22, 1987
INVENTOR(S) : Michel DESBOIS

It is certified that error appears in the above-identified patent and that said Letters Patent is hereby corrected as shown below:

In claim 1, Column 4, Line 34, change:

"leats" to --least--.

In claim 4, Column 4, Line 42, change:

"50 to 50 bars" to --5 to 50 bars--.

Signed and Sealed this

Twenty-ninth Day of March, 1988

Attest:

DONALD J. QUIGG

Attesting Officer

Commissioner of Patents and Trademarks